United States Patent [19]
Suokas et al.

[11] Patent Number: 5,741,954
[45] Date of Patent: Apr. 21, 1998

[54] PROCESS OF SELECTIVE DESULFONATION

[75] Inventors: Elias Suokas; Markku Niemi; Pekka Somersalo, all of Espoo; Jouko Kujala, Kokkola, all of Finland

[73] Assignee: Kemira Agro Oy, Espoo, Finland

[21] Appl. No.: 504,161

[22] Filed: Jul. 19, 1995

[30] Foreign Application Priority Data

Jul. 28, 1994 [JP] Japan ................................. 6-176550

[51] Int. Cl.$^6$ ........................... C07C 37/00; C07C 37/04
[52] U.S. Cl. ................................................ 568/795
[58] Field of Search ................................... 568/795

[56] References Cited

U.S. PATENT DOCUMENTS 4,475,002  10/1984  Wada et al. ........................ 568/795

FOREIGN PATENT DOCUMENTS

| 2362884 | 8/1974 | Germany. |
| 59-76033 | 4/1983 | Japan. |
| 1436369 | 5/1976 | United Kingdom. |

Primary Examiner—Marianne M. Cintins
Assistant Examiner—Dwayne C. Jones
Attorney, Agent, or Firm—Loeb & Loeb LLP

[57] ABSTRACT

This invention relates to a process for the preparation of m-alkylphenols, particularly of 3-ethylphenol, from the mixture of alkylbenzenesulfonic acid isomers by selective desulfonation, removal of formed alkylbenzene and caustic fusion. In the present invention the inventive desulfonation is accomplished by addition of steam to the mixture of sulfonic acid in an excess in relation to the amount of evaporable water, simultaneously maintaining the temperature of the mixture above 160° C. until the desired purity of isomers is obtained, and until the content of the sulfuric acid in the mixture is decreased below 40%.

3 Claims, No Drawings

PROCESS OF SELECTIVE DESULFONATION

BACKGROUND OF INVENTION

1. Field of the Invention

This invention relates to a process by which 3-alkylphenols can be prepared in high purity.

2. Description of Related Art

One known manner to produce 3-alkylphenols is sulfonation of alkylbenzene, isomerization of formed mixture of sulfonic acid isomers with heating into a mixture being rich in 3-alkylbenzenesulfonic acid and desulfonation (hydrolysis) of undesired o- and p-isomers back into alkylbenzene. The obtained, chiefly in the 3-position alkylated sulfonic acid is conventionally fused caustically into phenol. The literature describes different variations of this process, see for example German Patent No. 2 362 884 (Koppers Co.) and Japanese Patent Application No. 59 076033 (Taoka Chemical Co.). By this process, inter alia, 3-methylphenol, 3-ethylphenol, 3-isopropylphenol and 3,5-dimethylphenol can be produced.

However, the problem of known processes is to obtain a sufficiently selective desulfonation of the mixture of sulfonic acid because the sulfonation-desulfonation is a converse reaction and new undesired o- and p-isomers are formed continuously. Principally, this problem is solved by removal of alkylbenzene formed in the desulfonation with steam distillation in proportion as it is formed. This withdrawal is usually not sufficiently rapid and complete and for obtaining of highly pure 3-alkylphenol additional means are needed.

In the disclosure of the German Patent No. 2 363 884 desulfonated mixture of alkylbenzenesulfonic acid containing sulfuric acid is added to water and subsequently it is alkalized with lye and then distillation and caustic fusion are carried out.

Japanese Patent Application 59 076033 teaches that, if reaction mass is allowed to stand being hot after the desulfonation step, undesired isomers are formed in the reaction mixture impairing the purity of isomers of the end product. The above-mentioned application teaches also that in the high scale production the external cooling of reaction mass is not sufficiently rapid in order to obtain a good purity. In the Japanese Patent Application No. 59 067033 the problem of cooling is solved so that the hot (between 160° C. and 180° C.) slightly strong sulfuric acid containing mixture is cooled by adding water thereto so quickly as possible (during a period of an hour or suitably in an half hour) so that temperature of the mixture decreases to about 130° C. (between 20° and 150° C.). Subsequently alkali is added to the mixture and then caustic fusion is carried out. According to the Japanese Patent Application No. 59 076033 m/p ratio of ethylphenols is with internal cooling, when being the best, 96.5/3.5. With the external cooling, the ratio is clearly smaller, for example after 4 hours cooling to 130° C. the ratio is 91.5/8.5.

It is appreciable that purification of m-isomer from p-isomer with distillation is difficult and therefore starting mixture should be of good quality.

The process disclosed in the German Patent No. 2 362 884 follows, in regard to safety, a more recommended way to add slightly strong mixture of sulfuric acid to water while safety risks can be associated with the process of the Japanese Patent Application No. 59 076033 when water is added to the hot, slighly strong mixture of sulfuric acid. As to the ratio of isomers in the products of both processes there is still much to be desired for. Furthermore, in the process according to the Japanese Patent Application the ratio of isomers is susceptible to all delays which can easily occur in the industrial production.

SUMMARY OF THE INVENTION

Now it has been found that accomplishing the desulfonation of alkylbenzene and isomerization with heating e.g. in the conventional manner according to the above-mentioned references but changing conditions of the desulfonation, a more better m/p ratio of isomers than previously is obtained. For the mixture obtained with the novel manner of desulfonation, the manner of cooling is no more critical but external cooling can rather be used or the hot mixture can be directly discharged into water or mixture of lye for the following caustic fusion. In the novel manner of desulfonation the m/p ratio of product is not susceptible to delays possibly occurring in the process. Risks due to the rapid addition of water to hot sulfuric acid are also avoided with the novel manner of desulfonation.

The novel manner of desulfonation is characterized in that the mixture of alkylsulfonic acids being rich in m-isomers is selectively desulfonated by addition of hot steam to the mixture more than steam is removed from the mixture which steam takes simultaneously with it alkylbenzene formed in the desulfonation. The reaction mixture is kept continuously hot, at 160° C. or above, and desulfonation is continued until the desired ratio of m/p-isomers is achieved and until the content of sulfuric acid in the desulfonation mixture is on the level of 40% or below.

In m-alkylphenols to be prepared according to the invention, the alkyl component is preferably a lower alkyl, i.e. a $C_1$–$C_6$ alkyl, as for example methyl, ethyl or isopropyl, particularly preferably 3-ethylphenol is prepared.

Time needed for the desulfonation of sulfonic acids depends on details of the used equipment, and also on the temperature of desulfonation and the desired ratio of isomers. Extending the time of desulfonation and simultaneously retarding dilution, a better purity of isomers is obtained.

DESCRIPTION OF THE EMBODIMENT

The invention is illustrated in more detail by the following examples.

EXAMPLE 1

To 500 ml flask was added 150 mg (1.5 mol) 98% sulfuric acid and then, with mixing, 109 g (1.0 mol) ethylbenzene. Mixture was heated under reflux 3 hours increasing temperature gradually to 190° C. The mixture was heated at 190° C. 5 hours, whereby the ratio of m/p-isomers was 60/40. For the desulfonation, the mixture was cooled to about 170° C. and steam was conducted to the mixture. Steam distillation was continued 9 hours maintaining the temperature at about between 160° and 170° C. The content of $H_2SO_4$ in the mixture was 43.4% and the ratio of m/p-isomers 98/2. The mixture was cooled slowly externally 10° C. in an hour from the temperature of 160° C. to the temperature of 130° C. (cooling of 3 hours). After the cooling the ratio of m/p-isomers was 97.4/2.6.

It can be observed from the experiment that the ratio of isomers is better than that with external cooling or addition of water previously obtained. However, some isomerization has been occurréd when the content of sulfuric acid in the experiment is over 43%.

EXAMPLE 2

An experiment according to Example 1 was performed in production scale starting with 3300 kg 98% sulfuric acid.

The temperature in the sulfonation rose to 197° C., at which temperature the mixture was isomerized 5.5 hours. Steam was charged into the desulfonation during about 18 hours at the temperature of from 197° C. to 160° C. At the end of the desulfonation the ratio of m/p-isomers was 98.2/1.8 and when the mixture was externally cooled during 5.5 hours to the temperature of 50° C. the ratio of isomers was at the end the same 98.2/1.8, the content of sulfuric acid in the mixture being 39.2%.

It is observed from the experiment, that in the production scale with possibly cooling externally the ratio of isomers remains good and does not change when the content of sulfuric acid is below 40%.

EXAMPLE 3

In the experiment according to Example 1 desulfonation was continued until the ratio m/p-isomers was 97.9/2.1. The temperature was at the end of the desulfonation 160° C. and the content of sulfuric acid was 39.4%. The hot desulfonation mixture of 160° C. was poured to water. After dilution the temperature of aqueous mixture was 80° C. The m/p ratio in the mixture of alkylphenol, measured after the caustic fusion and acidification, was not changed.

It can be observed from the experiment, that the ratio of isomers does not change if the reaction mixture is directly discharged into water after the hydrolysis when being hot.

We claim:

1. A process for the preparation of m-ethylphenol from a hot mixture of sulfuric acid and ethylbenzenesulfonic acid isomers which is rich in the m-isomer, comprising the steps of:

(a) selectively desulfonating the isomers other than the m-isomer into ethylbenzene by addition of steam to the mixture and by removal of said ethylbenzene as formed from the mixture through desulfonation and .evaporable water, wherein the steam is fed to the mixture in excess of the amount of water evaporated from the mixture, wherein the desulfonation step is carried out at a temperature which is maintained above 160° C. during the desulfonation step, and which is decreased so as to reach a final temperature of 160° C. at the end of the desulfonation step, and wherein the content of sulfuric acid in the mixture is decreased during the desulfonation step to reach a final sulfuric acid concentration of less than 40%;

(b) mixing the hot reaction mixture with water after the desulfonation; and (c) caustically fusing the undesulfonated m-isomer of the ethylbenzenesulfonic acid contained in the mixture into m-ethylphenol.

2. The process according to claim 1, wherein the temperature of the reaction mixture when added to water is 160° C.

3. The process according to claim 1, wherein the hot reaction mixture is poured into water after the desulfonation.

* * * * *